US00RE38485E

(19) United States
(12) Reissued Patent
Busch

(10) Patent Number: US RE38,485 E
(45) Date of Reissued Patent: Apr. 6, 2004

(54) DRAPE FOR USE BY ANESTHESIA PROVIDER

(76) Inventor: Lyndon J. Busch, 3921 Overton Park East, Fort Worth, TX (US) 76109

(21) Appl. No.: 08/683,126

(22) Filed: Jul. 22, 1996

Related U.S. Patent Documents

Reissue of:
(64) Patent No.: 5,335,677
Issued: Aug. 9, 1994
Appl. No.: 07/850,599
Filed: Mar. 13, 1992

U.S. Applications:
(63) Continuation-in-part of application No. 07/626,620, filed on Dec. 7, 1990, now Pat. No. 5,156,167, and application No. 07/684,643, filed on Apr. 12, 1991, now Pat. No. 5,095,918.

(51) Int. Cl.[7] ..... A61B 19/08
(52) U.S. Cl. ..... 128/852; 128/855
(58) Field of Search ..... 128/852, 849, 128/855, 845, 846, 850, 851, 853, 854, 856

(56) References Cited

U.S. PATENT DOCUMENTS

| | | | |
|---|---|---|---|
| 3,347,544 | A | 10/1967 | Uffenorde |
| 3,537,446 | A | 11/1970 | Rowland et al. |
| RE27,710 | E | 7/1973 | Melges |
| 3,763,857 | A | 10/1973 | Schrading |
| 3,791,382 | A | 2/1974 | Collins |
| 3,856,005 | A | 12/1974 | Sislian |
| 3,889,667 | A | 6/1975 | Collins |
| 3,955,569 | A | 5/1976 | Krzewinksi |
| 4,027,665 | A | 6/1977 | Scrivens |
| 4,041,942 | A | 8/1977 | Dougan et al. |
| 4,058,112 | A | 11/1977 | Johnson |
| 4,275,720 | A | 6/1981 | Wichman |
| 4,323,062 | A | 4/1982 | Canty |
| 4,466,430 | A | 8/1984 | Shultz |
| 4,476,860 | A | 10/1984 | Collins et al. |
| 4,553,538 | A | 11/1985 | Rafelson |
| 4,553,539 | A | 11/1985 | Morris |
| 4,596,245 | A | 6/1986 | Morris |
| 4,720,881 | A | 1/1988 | Meyers |
| 4,976,274 | A | 12/1990 | Hanssen |

*Primary Examiner*—Michael A. Brown
(74) *Attorney, Agent, or Firm*—Grady K. Bergen; Robert H. Johnston, III

(57) ABSTRACT

A drape is shown for use by an anesthesia provided during a surgical procedure to temporarily hold accessories such as a suction instrument. The drape is adapted to be received on a patient support structure such as a hospital operating room table. The drape includes a main sheet of flexible, drapable material including a head region received beneath a patient's head having a pocket fold which defines an accessory receiving pocket. An envelope region is formed beneath the head region by folding a portion of the main sheet back upon itself. The envelope region defines a second accessory receiving pocket for the drape and further anchors the drape to the table during use. Subdivisions of the pocket folds provide smaller receptacles. Also provided are devices to adhere instruments in place and to secure the drape to its support. Additionally, methods of manufacture and use are included.

42 Claims, 9 Drawing Sheets

DRAPE FOR USE BY ANESTHESIA PROVIDER

Matter enclosed in heavy brackets [ ] appears in the original patent but forms no part of this reissue specification; matter printed in italics indicates the additions made by reissue.

BACKGROUND OF THE INVENTION

1. Field of the Invention

[The present application] *This application is a Reissue of Ser. No. 07/850,599 filed Mar. 13, 1992, now U.S. Pat. No. 5,335,677 which* is a continuation-in-part of U.S. Ser. No. 07/626,620 filed Dec. 7, 1990 now U.S. Pat. No. 5,156,167 and U.S. Ser. No. 07/684,643 filed [Jul. 30, 1991] *Apr. 12, 1991*, now U.S. Pat. No. 5,095,918 which are commonly owned and both of which are incorporated herein by reference.

The present invention relates generally to drapes of the type used in caring for a medical patient, such as during surgical procedures. More specifically, the invention relates to a drape used by an anesthesia provider during surgical procedures to temporarily hold accessories, such as a suction instrument, and to limit contamination.

2. Description of Prior Art

The practice of anesthesia today is a highly technical science involving myriad instrumentation. As a result, numerous items congest the work environment of the anesthesia provider. During any given surgical procedure, the anesthesia provider is surrounded by multiple electrical monitoring devices as well as machines which mix anesthetic gases, ventilate a patient's lungs, evacuate fluids, administer and warm fluids, and warm the patient's body. Because of the lack of a standardized receptacle or holder, items such as mediations, syringes, needles, and various tubings are not always within easy reach.

It is important to limit patient contamination of the work environment, personnel and subsequent patients. Suctioning saliva, blood, nasal secretions and gastric secretions potentiates contamination by these fluids and by infectious agents they may contain, such as hepatitis or the AIDS virus.

U.S. Pat. No. 4,720,881, issued Jan. 26, 1988, to Meyers, shows an anesthesia accessory unit which is a rigid tray assembly adapted to be supported on an end portion of a patient's bed structure, normally a hospital operating room table. While this device offers a number of convenient receptacles, it is non-disposable and relatively expensive to manufacture. Also, the receptacle areas are not provided in the form of clean or sterile pockets which could be closed about the contaminated portion of a surgical instrument to prevent contamination of surrounding work areas, personnel, or subsequent patients.

A disposable drape, particularly adapted for receiving anesthesia accessories, could be inexpensively produced. Intended for only a single use, it would not need to be laundered or re-sterilized. Use of disposable drapes has increased in recent years. However, Applicant is unaware of any drapes that have been tailored specifically to hold anesthesia instruments during surgical procedures to limit contamination.

The present invention provides an accessory holder for a medical care provider, such as an anesthesia provider, in the form of a disposable drape adapted to be received on an end of a patient support structure, such as a hospital operating room table. Additionally, the invention provides such a drape having accessory receiving pockets which define clean or sterile enclosures for temporarily holding a variety of accessories and instruments during surgical procedures.

Another feature of the invention is a disposable drape having pockets for receiving a suction instrument during anesthetic procedures. The pockets provide a sterile environment for the instrument and thus limit or avoid, contamination of the surrounding work area, personnel, or subsequent patients.

The invention could decrease or eliminate the need for an assistant to the anesthesia provider. Potentially the drape could improve the dexterity of the anesthesia provider by providing a convenient clean or sterile receptable for anesthesia accessories, thus freeing a hand during surgical procedures.

Finally, the invention provides an accessory drape installable upon a variety of hospital operating room tables, stretchers and patient supports of various manufacturers' designs, so that the accessory drape can be standardized from one operating room to another.

SUMMARY OF THE INVENTION

The invention is intended for use by a medical care provider, such as an anesthesia provider, during surgical procedures. Adapted for reception on a patient support structure, the drape includes a main sheet of flexible, drapable material. The main sheet has a first region adapted to receive a part of the patient, usually the head, when the patient is received on the support structure. This anchors the drape. The first region includes a pocket fold which defines a first accessory receiving pocket. An envelope region is formed beneath the first region of the drapable material and defines a second accessory receiving. The envelope region is adapted to receive a part of the support structure to further anchor the drape.

The first accessory receiving pocket has a top layer and a bottom layer, each of which has a front edge, a rear edge and opposing side edges. The front edge of the top layer may be recessed to facilitate insertion of accessories within the pocket during surgical procedures. Preferably, the drape includes at least one additional accessory receiving pocket formed by a pocket fold in the main sheet. The additional pocket is arranged to depend downwardly from the first or head region of the drape, generally perpendicular to the plane thereof when the drape is received on the support structure.

The drape is particularly suited to temporarily hold a suction instrument during surgical procedures. In such an embodiment, the drape is received on a hospital operating room table. Additionally, the drape could provide multiple pockets. Although the pockets could be oriented with an opening at any convenient location, a preferred embodiment orients the opening upward.

By including an aperture in the drape, other useful configurations are possible. For example, the patient's head could be received through an aperture and a panel of the drape could then be elevated to form an ether screen. Additional features and advantages will be apparent in the written description which follows.

BRIEF DESCRIPTION OF THE DRAWINGS

in FIG. 1 showing the first accessory receiving pocket, envelope region and one additional accessory receiving pocket with the folds being exaggerated for ease of illustration;

in FIG. 5;

in FIG. 7;

in FIG. 9;

DETAILED DESCRIPTION OF THE INVENTION

Figure 1:
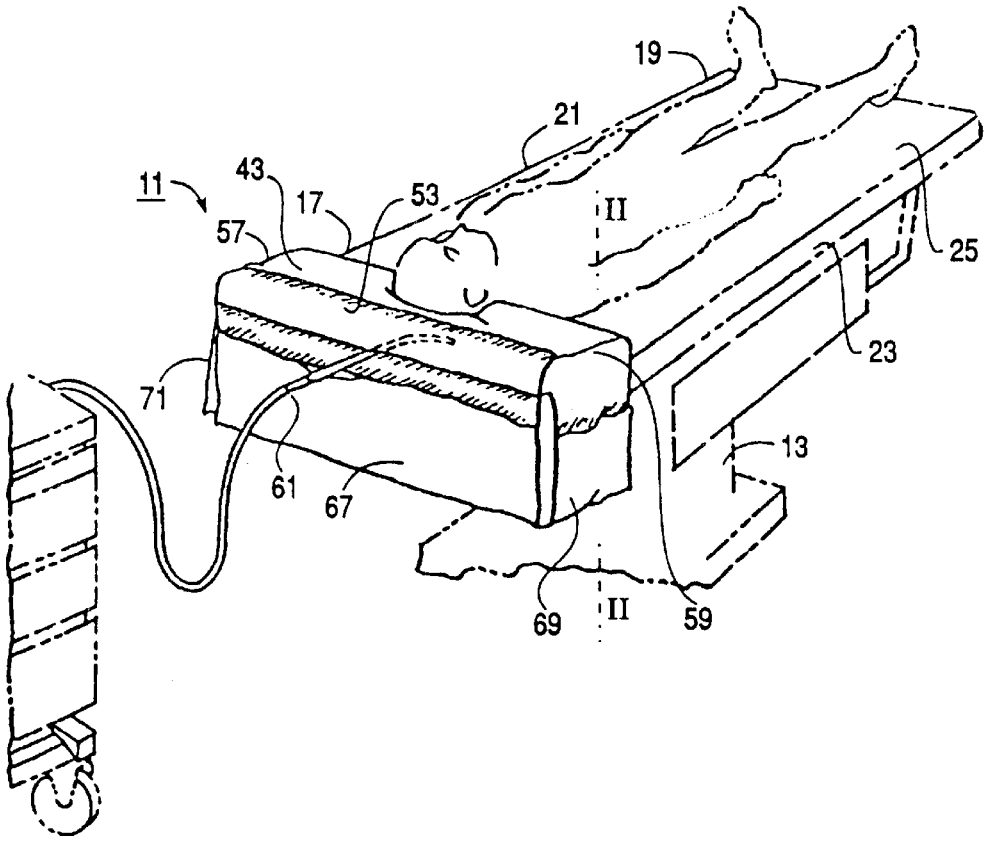
FIG. 1 is a simplified, perspective view of a patient support structure, in this case a hospital operating room table, showing the accessory drape of the invention installed at the head of the table, the drape being used to receive a suction instrument of the type used during a surgical procedure.

FIG. 1 shows an accessory drape 11 which is intended for use by a medical care provider, such as an anesthesia provider (anesthesiologist or anesthetist), during surgical procedures. These procedures may occur in an operating room, emergency room or in any other area where anesthetic accessories, such as a suction instrument, are used. The primary purpose of drape 11 is to reduce contamination of the surrounding area and/or personnel due to body fluids which occur in routine anesthetic practice. Examples include use of a suction apparatus to suction the oral cavity, nasal passages and the stomach.

Accessory drape 11 is adapted to be received on a patient support, typically a hospital operating room table, such as table 13 shown in FIG. 1. Accessory drape 11 can also be utilized on other patient supports, such as a stretcher, a gurney, or a chair. A number of operating room tables are available commercially with either moveable or fixed bases. The fixed-base table is typically available with interchangeable table tops to meet the needs of specific surgical specialties and will be familiar to those skilled in the art. The standard operating room table has three or more hinged sections including a head support (shown in isolated fashion as 15 in FIG. 2) that can be pivoted or flexed at hinged locations. Special operating tables are available, e.g., genitourinary, orthopedic and ophthalmologic surgery.

As seen in FIG. 1, support structure 13 may include a head 17, a foot 19 and opposing sides 21, 23 which define a horizontal plane 25 of rest for a patient (shown in dotted lines in FIG. 1). Head support 15 located at head 17 of table 13 can be a cushion which elevates the patient's head slightly above horizontal plane 25. The cushion is usually pivotable about an axis which is approximately transverses the patient's neck region.

Figure 3:
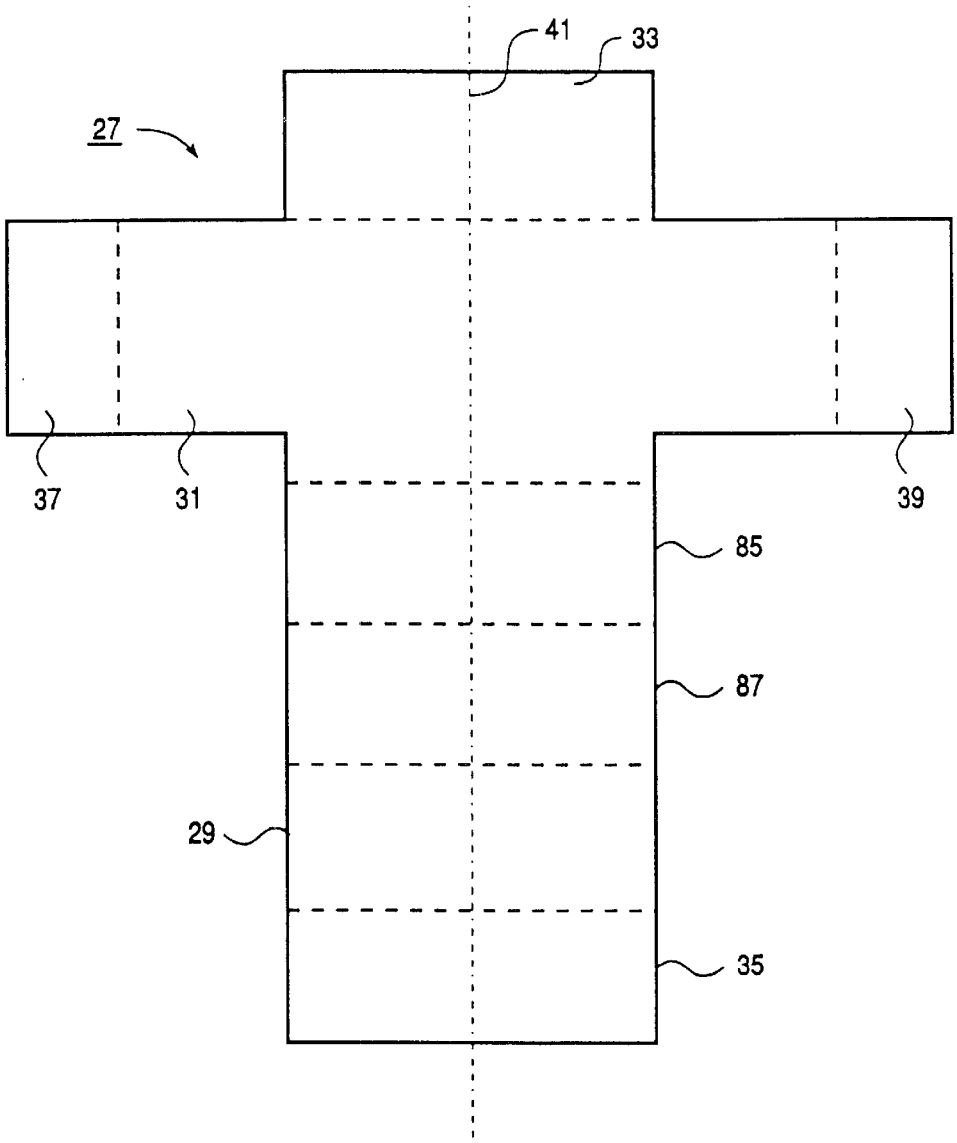
FIG. 3 is a plan view of the main sheet of flexible, drapable material used to form the accessory drape of the invention.
Figure 11:
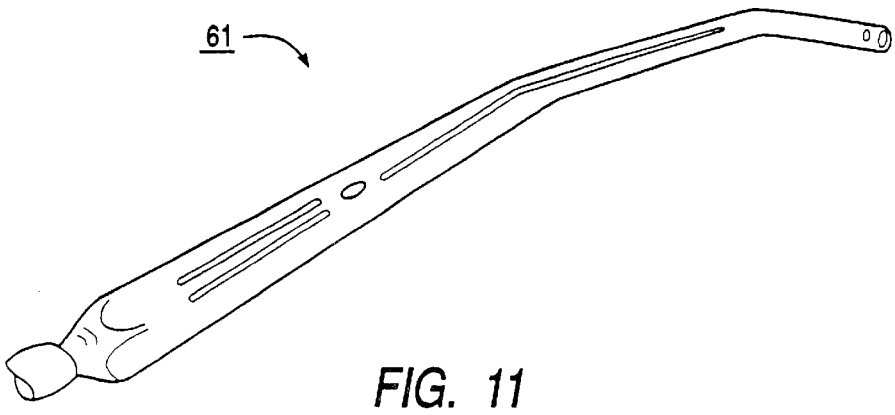
FIG. 11 is a perspective view of a suction instrument of the type which can be stored within the pockets of the drape of the invention.
Figure 4:
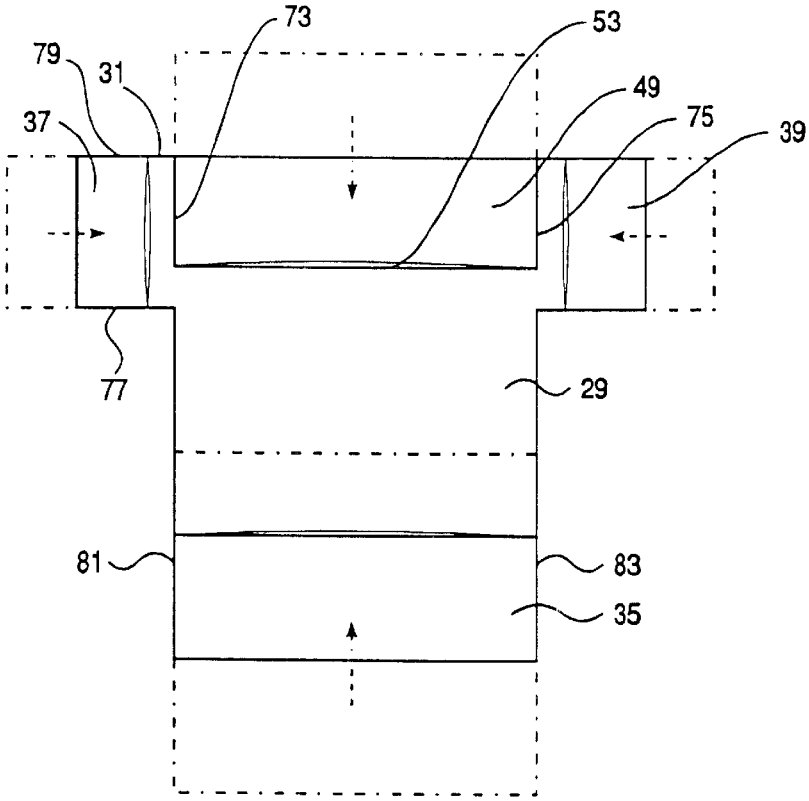
FIG. 4 is a view similar to FIG. 3 showing the initial folds used to form the accessory receiving pockets.
Figure 5:
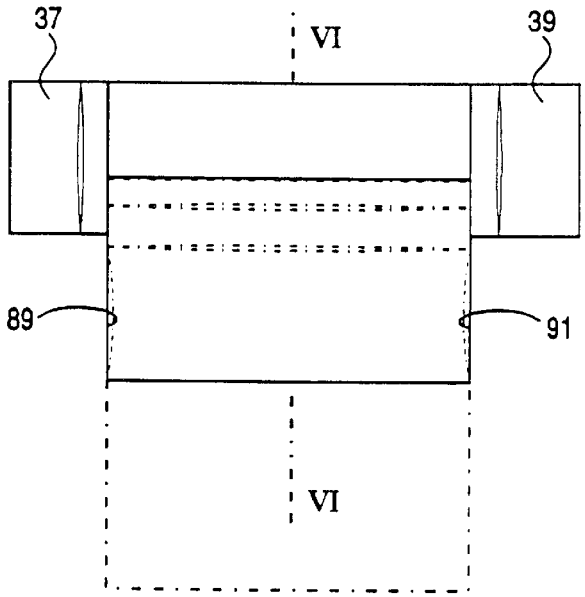
FIG. 5 is a plan view, similar to FIG. 4, showing the fold used to form the envelope region of the accessory drape.
Figure 6:
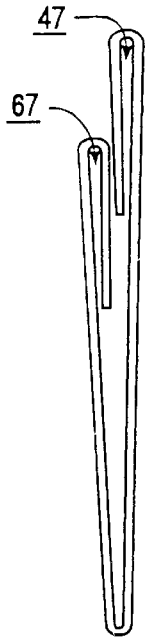
FIG. 6 is a cross-sectional view taken along lines VI.—VI.
Figure 7:
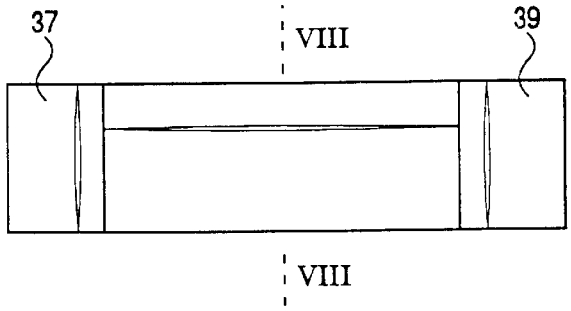
FIG. 7 shows the accessory drape folded in convenient fashion for sterile packaging.
Figure 8:
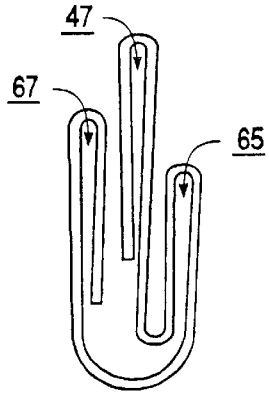
FIG. 8 is a cross-sectional view taken along lines VIII.—VIII.

As best seen in FIG. 3, drape 11 is formed from a main sheet of flexible, drapable material 27. A number of flexible materials can conveniently be utilized for this purpose including cloth, thin plastic and even paper. If cloth or paper materials are utilized, they are preferably formed from a water proof material which forms a moisture barrier to prevent fluids present in any accessory pockets from penetrating the material of drape 11. This can be accomplished in a number of manners, including a thin plastic layer sandwiched between upper and lower cloth or paper layers, spraying or coating water previous materials with a moisture barrier material, or forming the drape entirely from a water impervious material.

As shown in FIG. 3, main sheet 27 of flexible, drapable material initially forms a cross-shaped panel of material, the panel having a longitudinal body portion 29 and a cross-arm portion 31 arranged transversely thereto. Longitudinal body portion 29 includes a top panel 33 and a bottom panel 35, cross-arm portion 31 including outer panels 37, 39 arranged perpendicular to longitudinal axis 41 of body portion 29.

Figure 2:
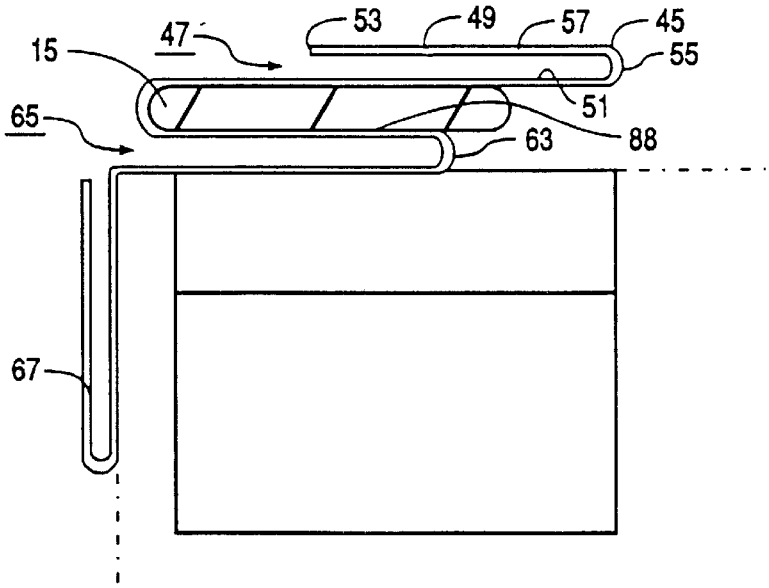
FIG. 2 is a simplified view, taken along lines II.—II.
Figure 9:
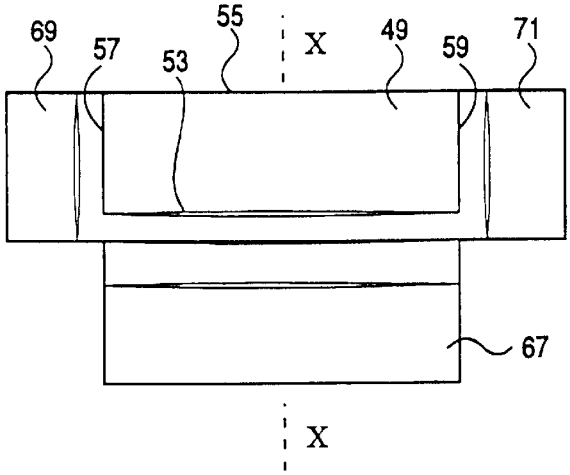
FIG. 9 is a top, plan view of the completed accessory drape of the invention showing the completed folds.

As shown in FIG. 1, main sheet 27 has a first or head region 43 which is adapted to be received beneath a patient's head when the patient's head is received on head support 15 (FIG. 2) for anchoring drape 11 to operating table 13. As best seen in FIG. 2, head region 43 includes a pocket fold 45 which defines a first accessory receiving pocket 47 for drape 11. First accessory receiving pocket 47 has a top layer 49 and a bottom layer 51. Top layer 49 and bottom layer 51 each have a front edge 53, a rear edge 55 and opposing side edges 57, 59, respectively (see FIG. 9). Front edge 53 of top layer 49 is recessed to facilitate the insertion of accessories, such as a commercially available suction instrument (61 in FIG. 1).

An envelope region 63 is formed beneath first or head region 43 (FIG. 1) of the drapable material. Envelope region 43 defines a second accessory receiving pocket 65 for drape 11. Envelope region 63 is adapted to be received beneath patient head support 15 which further anchors drape 11 to table 13.

As shown in FIGS. 1 and 2, drape 11 preferably includes at least one additional accessory receiving pocket 67 formed by a pocket fold in main street 27. An additional accessory receiving pocket 67 is arranged to depend downwardly from head region 43 of drape 11 generally perpendicular to the plane thereof when drape 11 is received on operating table 13. If desired, additional accessory receiving pockets 69, 71 can be provided which depend downwardly from head region 43 of drape 11 on each of opposing sides 21, 23 of table 13, adjacent head 43 thereof. Each additional accessory pocket 69, 71 is arranged generally perpendicular to horizontal plane 25 of the support structure.

As shown in FIGS. 3–10, drape 11 can be simply and economically formed from the initially cross-shaped piece of material forming main sheet 27. Head region pocket fold 45 is formed by folding top panel 33 in the direction of cross-arm portion 31 (indicated by arrows in FIG. 4), thereby overlaying cross-arm portion 31 a selected distance. Seams 73, 75 can be provided along either of the opposing side edges, as by heat sealing, sewing or gluing. Outer panels 37, 39 are folded back in the direction of longitudinal body portion 29 to form additional accessory pockets. Bottom panel 35 of longitudinal body portion 29 has a lower most extent which is folded back in the direction of cross-arm portion 31 to form an additional accessory pocket (see FIG. 4). The accessory pockets also have side seams, e.g., 77, 79, 81, 83.

Figure 10:
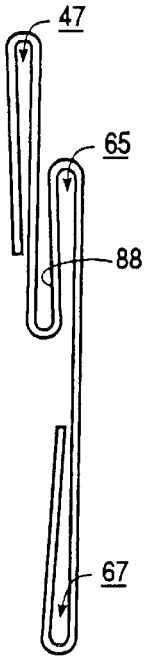
FIG. 10 is a cross-sectional view taken along lines X.—X.

Envelope region 63 can conveniently be formed in main sheet 27 by folding a first selected length (85 in FIG. 3) back upon a second selected length 87 to create and instrument receiving pocket 65. Pocket 65 can also be provided with side seams 89, 91 (shown by dotted lines in FIG. 5). As shown in FIGS. 2 and 10, top layer 88 of envelope region 63 is received beneath patient head support 15 to further anchor drape 11 to table 13.

Figure 12:
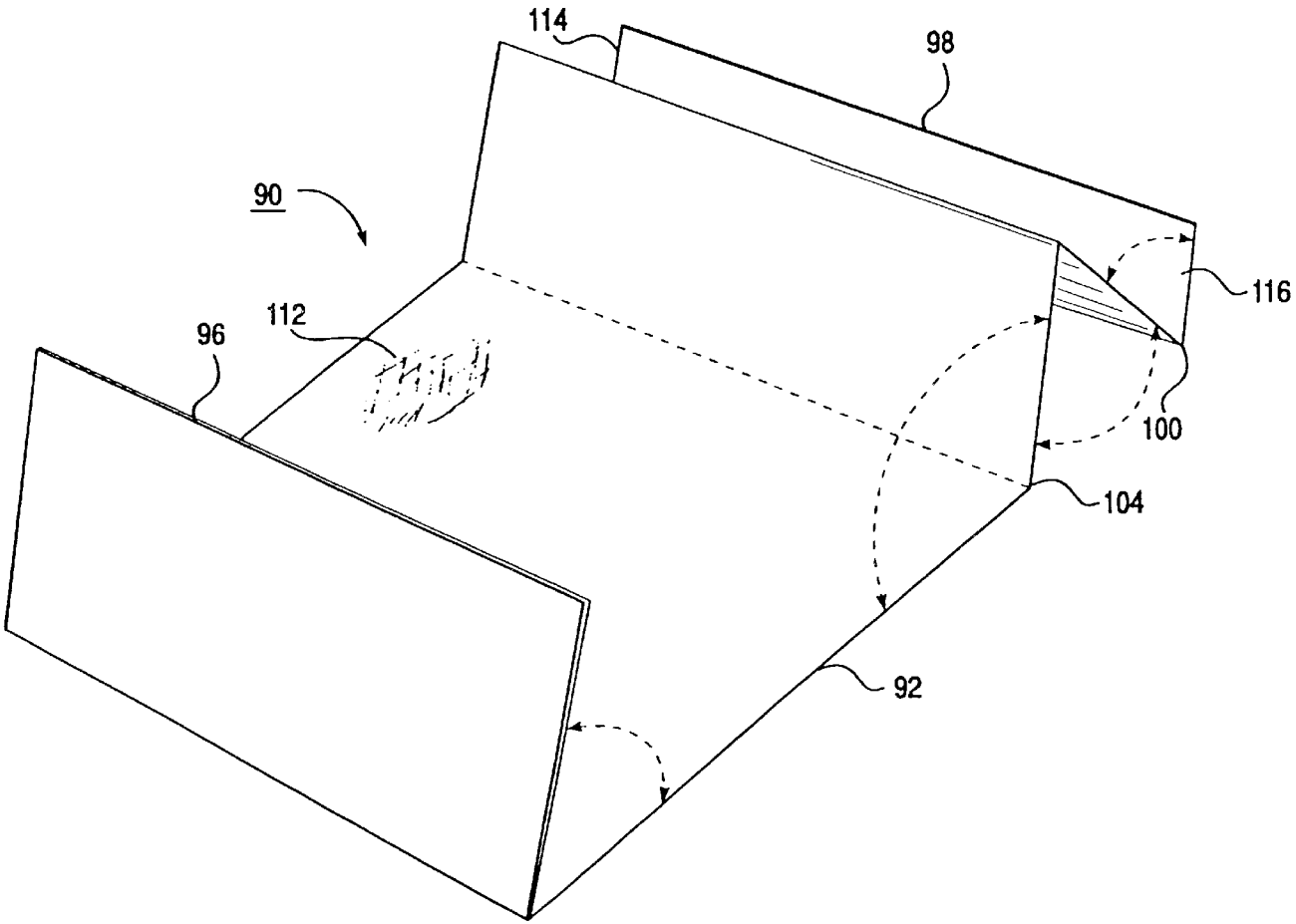
FIG. 12 illustrates another embodiment of the invention in which the main sheet of flexible, drapeable material is provided as a generally rectangular panel one end of which is folded to form a hemmed pocket and having an opposite, free extent.

FIG. 12 shows another embodiment 90 in which a main sheet of flexible, drapeable material 92 initially forms a generally rectangular panel with a hemmed pocket 94 (FIG. 13) formed on an end 96 thereof and having a free extent 98 opposite hemmed pocket 94. First and second accessory receiving pockets are formed by repetitively folding free extent 98. Thus main sheet 92 is folded (FIG. 12) to form a first fold 100 which defines a first accessory receiving pocket 102, Main sheet 92 is folded again to form a second fold 104 beneath first accessory receiving pocket 102, the second fold 104 defining a second accessory receiving pocket 106.

Drape 90 is used by placing first accessory receiving pocket 102 beneath the head of patient when the patient's head is received on a head support 108. This anchors drape 90 to the support structure. Second accessory receiving pocket 106 is placed beneath head support 108 drape 90.

Figure 13:
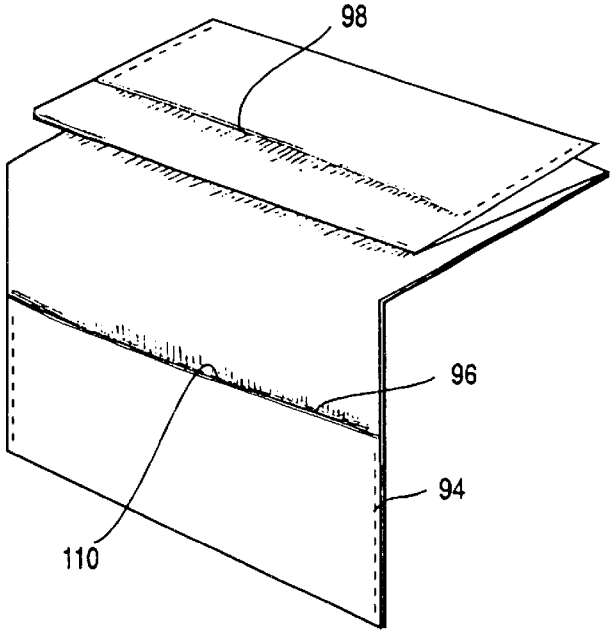
FIG. 13 illustrates the method by which the first and second accessory receiving pockets are formed by repetitively folding the free extent of the main sheet of drapeable material.
Figure 14:
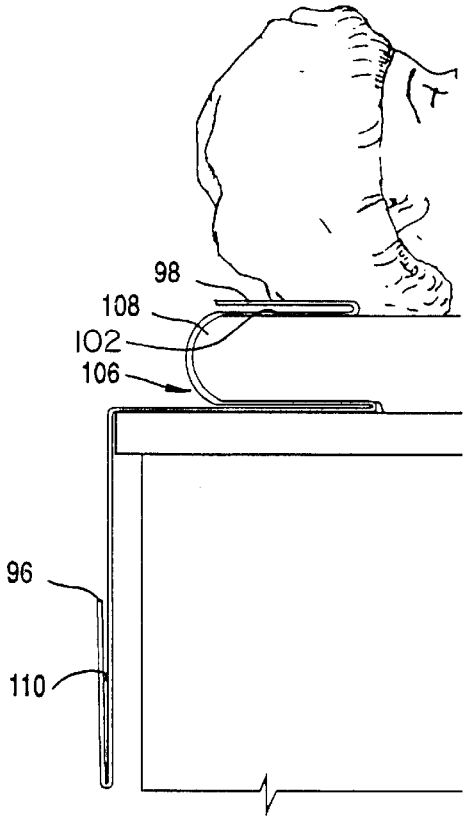
FIG. 14 is a view of the head support of a hospital operating room table showing the drape of FIG. 12 installed thereon.

As shown in FIGS. 13 and 14, drape 90 is preferably provided with a third accessory receiving pocket 110 formed by hemmed pocket 94. Pocket 110 is arranged to depend downwardly from main sheet 92 generally perpendicular thereto when the drape is received on the support structure.

Drape 90 is preferably formed from a waterproof material which forms a moisture and biological barrier to prevent fluids present in the accessory pockets from penetrating the material. At least one of the accessory receiving pockets 102, 106, 110 can also be provided with an absorbent lining (shown as 112 in FIG. 12) for containing contamination within the respective accessory receiving pocket. For instance, absorbent lining 112 could comprise a foam lining which could be used to remove some of the gross contamination from the suction device when the device is placed within the pocket. Absorbent material 112 can conveniently be absorbent paper, cloth, sponge or similar material. Any material which serves to contain such contamination, or which can be lined to contain such contamination, can be utilized.

Because an object of the invention is to limit contamination and the spread of infectious agents, the drape is preferably provided with at least selected regions formed of a material which will contain contaminants. A variety of suitable materials can be utilized which will be familiar to those in the disposable surgical drape industry. Examples include paper, cloth, plastic, polymer coated paper, or other material which serve a similar function.

Figure 15A:
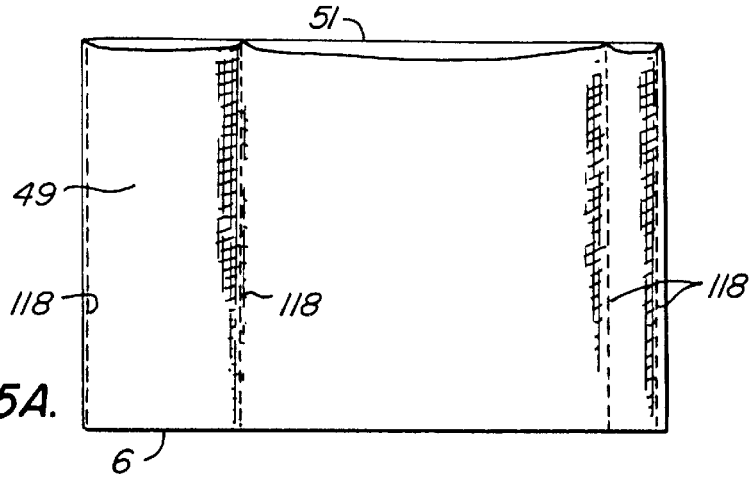
FIGS. 15abc are plan views showing alternative pockets.
Figure 15B:
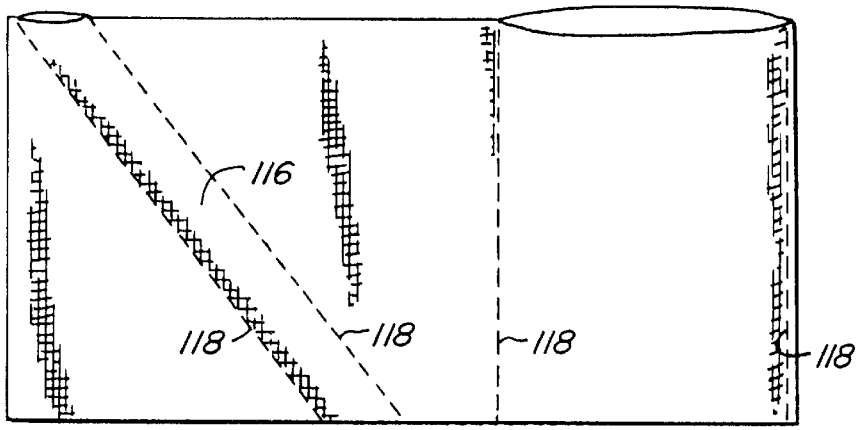
Figure 15C:
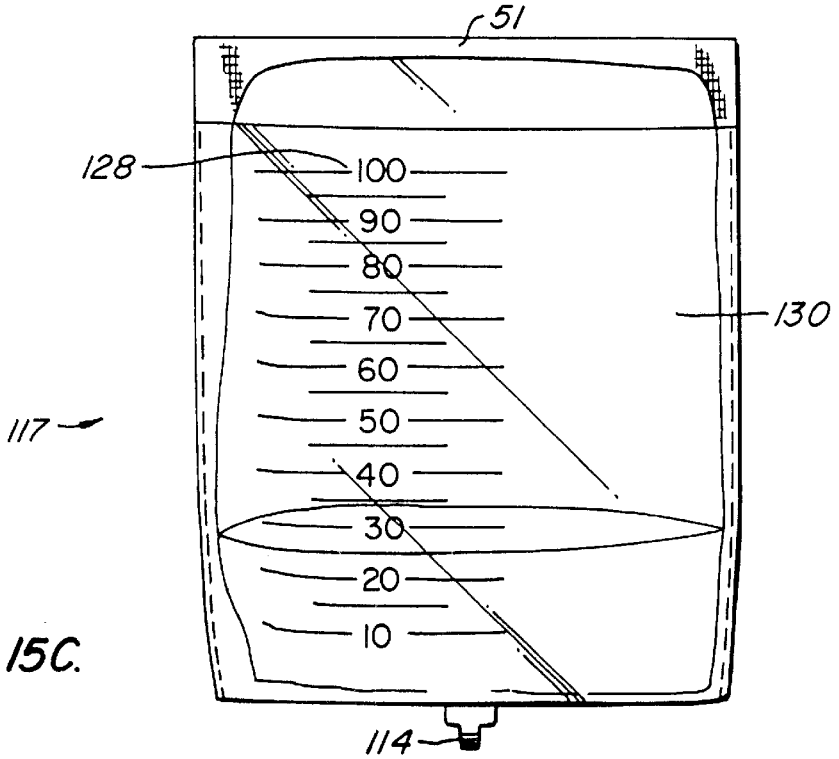
Figure 16:
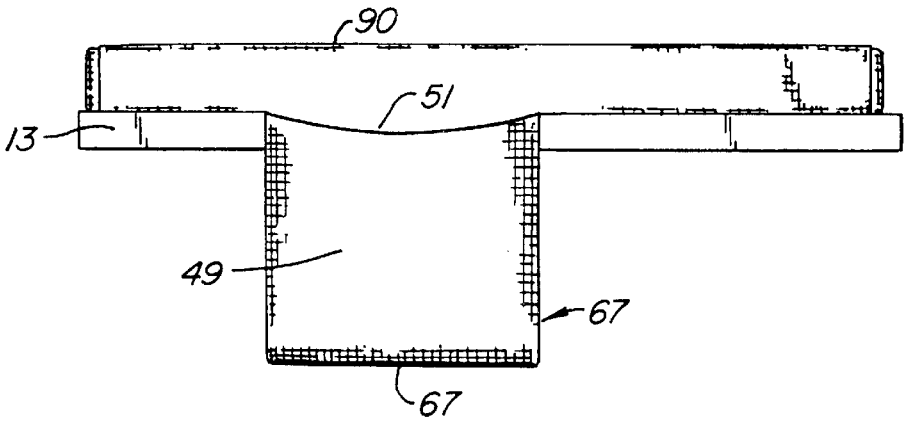
FIG. 16 is a plan view showing eccentrically placed pockets.
Figure 17A:
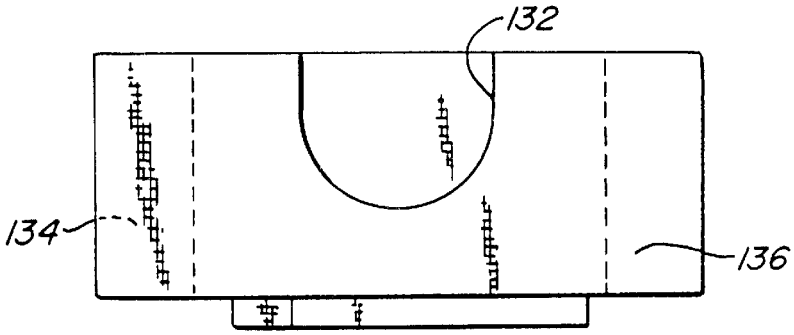
FIG. 17ab is an embodiment including an aperture to receive a patient's head and an ether screen barrier.
Figure 17B:
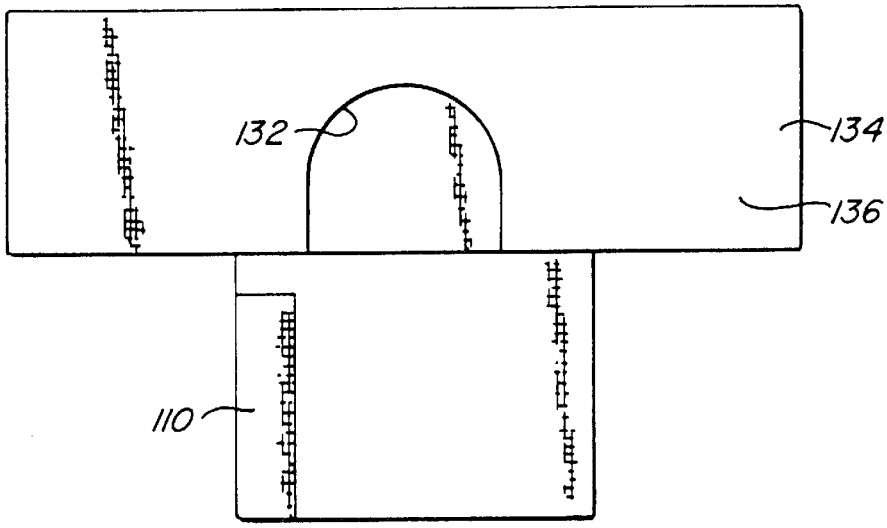
Figure 18A:
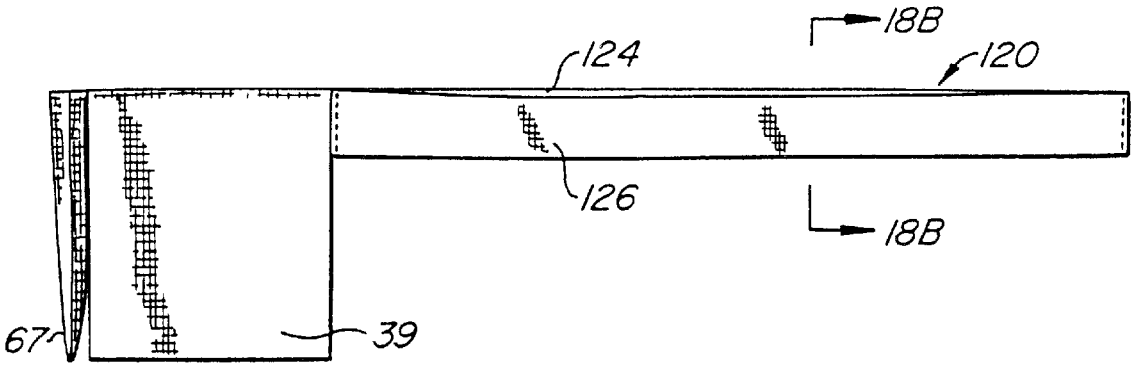
FIG. 18ab is an embodiment having gutters along a portion of the drape depending over the dies of the table.
Figure 18B:
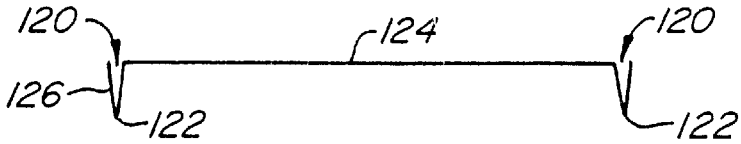

Alternative embodiments will be apparent to the artisan. For example, FIG. 15b shows an angled holster pocket. FIG. 15c shows a pocket having a transparent face with calibration marks. A pocket may be conveniently placed off center as in FIG. 16. This arrangement allows placement of a tube holder or so-called "Christmas tree" to one side of the pocket.

Additional features could be added without departing from the scope of the invention. Means for securing a suction tube to the drape or for adhering accessories to the drape could be included. For instance, a loop or series of loops may provide such means. Also, a Velcro™ patch or strip could be used to secure an accessory, such as a tray. An alternative embodiment could provide to further secure the drape to the mattress. For example, a portion of the drape could be cut away from the area which would cover a Velcro™ patch which some manufacturers provide to secure the mattress to the table. On the other hand, the drape could be adapted to receive the mattress in addition to the table.

Although the invention has been in described in its preferred form, a number of modifications can be envisioned which fall within the scope of the present invention. For instance, for use in a dental office, the accessory drape might be oriented other than at the extreme head of the bed with the envelope region continuing to be received between the cushion and the patient support structure. The accessory drape could also be equipped with other clamps and receptacles to, for instance, crimp off the suction tubing to reduce noise.

The invention has several advantages. The accessory drape is simple in design and economical to manufacture. It can be made disposable, thus eliminating laundering and sterilizing drapes for re-use. A plurality of accessory pockets are included for receiving instruments, such as a suction device, to reduce contamination of the operating room environment and/or operating room personnel, or subsequent patients, with body fluids which occur in the routine use of suction devices during surgical procedures. The accessory pockets provide a secure means for retaining a variety of surgical instruments while isolating the instruments in sterile fashion.

The drape is conveniently received on a region, usually the head region, of a variety of patient support structures. Such structures include operating tables, emergency room tables, stretchers and gurneys as well as chairs for specialized purposes, such as dental procedures. The drape reduces contamination of the surrounding area and reduces the chance of exposure of a care-giver, or of a subsequent patient, to a variety of patient contaminants.

While the invention is described in some detail with specific reference to a preferred embodiment and certain alternatives, the invention is not limited to that embodiment or those alternatives. Artisans of ordinary skill will appreciate other alternatives within the scope of the invention. The scope of the invention is defined not by the foregoing description, but by the following claims.

What is claimed is:

1. A surgical drape for use on a patient support structure, the drape comprising:

a main sheet of flexible, drapable material having first, second and third regions;

the first region adapted to receive at least part of a patient, and including a first fold for receiving accessories;

the second region including a second and a third fold, said second and third folds adapted to be arranged below the part of the patient received by the first region, and second fold defining a pocket adapted to receive at least part of the support structure and said third fold defining an accessory receiving pocket, wherein the opening of the accessory receiving pocket defined by the third fold is open in a direction opposite to the opening of the pocket defined by the second fold, and wherein one of the pockets is directly on top of the other pocket; and the third region adapted to depend downwardly from the support structure when the drape is received on the support structure, including a fourth fold for receiving an item.

2. The drape of claim 1 wherein the third region is adapted for receiving an accessory.

3. The drape of claim 1 wherein the third region is adapted for receiving a liquid.

4. The drape of claim 1 wherein the third region includes a sealed portion such that an opening remains thereby creating a pocket.

5. The drape of claim 4 wherein the sealed portion is oriented substantially perpendicular to the fold of the second region.

6. The drape of claim 4 wherein the pocket includes a transparent member such that visualization of an interior of the pocket is possible.

7. The drape of claim 1 further comprising an aperture.

8. The drape of claim 7 wherein the aperture is adapted to receive the patient's head therethrough.

9. The drape of claim 7 further comprising a fourth region adjacent to the aperture adapted for use as an ether screen.

10. A method of receiving an item into a surgical drape, said method comprising:

selecting a flexible drapable material provided with at least four folds;

installing the material onto a patient support structure such that a portion of the first fold receives a portion of the support structure and a portion of the second fold is beneath the support structure;

placing a portion of a patient onto a portion of the drape such that the second and third folds are anchored by that portion of the patient and are arranged below that portion of the patient; and arranging the fourth fold to depend downwardly from the support structure.

11. The method of claim 10 further comprising the step of selecting a drapable material having said folds wherein at least one of the folds includes a sealed portion such that an opening remains creating a pocket.

12. The method of claim 11 wherein the pocket is used to receive an anesthetic accessory.

13. The method of claim 11 wherein the pocket is used to receive a bodily liquid from the patient.

14. The method of claim 10 wherein the drapable material includes an aperture to receive a portion of the patient therethrough.

15. The method of claim 14 wherein the part of the patient received through the aperture is the patient's head and further comprising step of utilizing a part of the drapable material to function as an ether screen.

16. The surgical drape of claim 4 wherein the sealing is accomplished by heat.

17. The surgical drape of claim 4 wherein the sealing is accomplished by sewing.

18. The surgical drape of claim 4 wherein the sealing is accomplished by gluing.

19. A surgical drape for use on a patient support structure, the drape comprising:

a main sheet of flexible, drapable material having first, second and third regions;

the first region adapted to receive at least part of a patient, and including a fold defining an accessory receiving pocket;

the second region adapted to receive at least part of the support structure and having a fold defining a pocket, wherein the opening of the pocket is open in a direction opposite to the opening of the accessory receiving pocket, and wherein one of the pockets is directly on top of the other pocket;

the third region adapted to depend downwardly from the support structure when the drape is received on the support structure; and an aperture adapted to receive a part of a patient therethrough.

20. The drape of claim 19 wherein the aperture is adapted to receive the patient's head therethrough.

21. A method of receiving an item in a surgical drape, said method comprising:

selecting a flexible, drapable material provided with at least three folds and an aperture to receive a portion of the patient therethrough;

installing the material onto a patient support structure, such that a portion of the first fold receives a portion of the support structure;

placing a part of a patient onto a portion of the drape such that the second fold is anchored by that part of the patient; and arranging the third fold to depend downwardly from the support structure.

22. The method of claim 21 wherein the part of the patient received through the aperture is the patient's head and further comprising the step of utilizing a portion of the drapable material to function as an ether screen.

*23. A surgical drape for use on a patient support structure, the drape comprising:*

*a sheet of flexible, drapable material including a top edge and a bottom edge separated between two side edges, the sheet having a first region, a second region and a fold generally perpendicular to the two side edges and between the first and second regions with the first region to the top edge direction of the fold and the second region to the bottom edge direction;*

*the first region adapted to receive at least part of a patient; and*

*the second region adapted to be arranged below the part of the patient received by the first region, wherein the fold defines an anesthesia accessory receiving area adapted to receive an item.*

*24. The drape of claim 23 in which the first and second regions are adapted for receiving a liquid.*

*25. The drape of claim 23 in which the side edges are sealed such that an opening generally remains between the top edge and bottom edge thereby creating a pocket.*

*26. The drape of claim 25 wherein the sealing is accomplished by heat.*

*27. The drape of claim 25 wherein the sealng is accomplished by sewing.*

*28. The drape of claim 25 wherein the sealing is accomplished by gluing.*

*29. A surgical drape for use on a patient support structure, the drape comprising:*

*a main sheet of flexible, drapable material having first and second regions;*

*the first region adapted to receive at least part of a patient, and including a first fold for receiving accessories; and*

*the second region including a second and a third fold, said second and third folds adapted to be arranged below the part of the patient received by the first region, said second fold defining a pocket adapted to receive at least part of the patient support structure and said third fold defining an acessory receiving pocket, wherein the opening of the accessory receiving pocket defined by the third fold is open in a direction opposite to the opening of the pocket defined by the second fold, and wherein one of the pockets is directly on top of the other pocket.*

*30. The drape of claim 29 in which the second region is adapted for receiving a liquid.*

*31. The drape of claim 29 in which third fold in the second region includes a sealed portion such that an opening remains thereby creating a pocket.*

*32. The drape of claim 31 wherein the sealing is accomplished by heat.*

*33. The drape of claim 31 wherein the sealing is accomplished by sewing.*

*34. The drape of claim 31 wherein the sealing is accomplished by gluing.*

*35. A surgical drape for use on a patient support structure, the drape consisting essentially of:*

*a main sheet of flexible, drapable material having a first region to receive at least part of a patient onto the first region, and including a first fold for receiving accessories.*

*36. The drape of claim 35 in which the first region is adapted for receiving a liquid.*

*37. The drape of claim 35 in which the first region includes a sealed portion such that an opening remains thereby creating a pocket.*

*38. The drape of claim 37 wherein the sealing is accomplished by heat.*

*39. The drape of claim 37 wherein the sealing is accomplished by sewing.*

*40. The drape of claim 37 wherein the sealing is accomplished by gluing.*

*41. A method of receiving an item into a surgical drape for use on a patient support structure, said method steps consisting essentially of:*

*selecting a flexible, material provided with at least one fold;*

*installing the material onto the patient support structure; and*

*placing a part of a patient onto a portion of the drape so that a first fold is anchored by that part of the patient.*

*42. A method of receiving an item into a surgical drape for use on a patient support structure, said method steps consisting essentially of:*

*selecting a flexible, drapable material provided with at least two folds;*

*installing the material onto the patient support structure, such that a first fold is placed on a top surface of the patient support structure and a second fold is placed under a lower surface of the patient support structure; and*

*placing a part of a patient onto a portion of the drape so that the first fold is anchored by that part of the patient.*

* * * * *